United States Patent [19]

Walasek et al.

[11] Patent Number: 5,035,241
[45] Date of Patent: Jul. 30, 1991

[54] REUSABLE AND MICROWAVABLE HOT INSULATED COMPRESS AND METHOD OF MANUFACTURE

[75] Inventors: Steven P. Walasek; Stuart J. Walasek, both of Shavertown, Pa.

[73] Assignee: Packaging Electronics & Devices Corp., Nanticoke, Pa.

[21] Appl. No.: 448,864

[22] Filed: Dec. 12, 1989

[51] Int. Cl.$^5$ ............................................. A61F 7/08
[52] U.S. Cl. ..................................... 128/403; 62/530
[58] Field of Search ............... 128/379, 380, 402, 403, 128/400; 62/630, 259.3; 383/901

[56] References Cited

U.S. PATENT DOCUMENTS

| | | | |
|---|---|---|---|
| 2,562,121 | 7/1951 | Poux | 128/402 |
| 3,763,622 | 10/1973 | Stanley, Jr. | 53/25 |
| 3,780,537 | 12/1973 | Spencer | 62/530 |
| 3,804,077 | 4/1974 | Williams | 126/263 |
| 3,874,504 | 4/1975 | Verakas | 206/219 |
| 3,885,403 | 5/1975 | Spencer | 62/530 |
| 3,889,684 | 6/1975 | Lebold | 128/402 |
| 3,893,834 | 7/1975 | Armstrong | 62/4 |
| 4,055,188 | 10/1977 | Pelton | 128/402 |
| 4,092,982 | 6/1978 | Salem | 128/82.1 |
| 4,114,620 | 9/1978 | Moore et al. | 128/254 |
| 4,243,041 | 1/1981 | Paul | 128/402 |
| 4,381,025 | 4/1983 | Schooley | 150/2.4 |
| 4,404,820 | 9/1983 | Romaine | 62/530 |
| 4,462,224 | 7/1984 | Dunshee et al. | 62/530 |
| 4,488,552 | 12/1984 | McCann et al. | 128/402 |
| 4,576,169 | 3/1986 | Williams | 128/402 |
| 4,596,250 | 6/1986 | Beisang, III et al. | 128/402 |
| 4,641,655 | 2/1987 | Abt | 62/259.3 |
| 4,671,267 | 6/1987 | Stout | 128/156 |
| 4,676,247 | 6/1987 | Van Cleve | 128/402 |
| 4,688,572 | 8/1987 | Hubbard et al. | 383/901 |
| 4,756,311 | 7/1988 | Francis, Jr. | 128/403 |
| 4,981,135 | 1/1991 | Hardy | 128/402 |

FOREIGN PATENT DOCUMENTS

| | | | |
|---|---|---|---|
| 1383536 | 2/1975 | United Kingdom . | |
| 2160965 | 1/1986 | United Kingdom | 383/901 |

Primary Examiner—Edward M. Coven
Assistant Examiner—Mark S. Graham
Attorney, Agent, or Firm—Joseph Scafetta, Jr.

[57] ABSTRACT

A reusable and microwavable hot insulated compress has a bottom laminate, a first pocket containing a gel, a middle laminate being positioned above the first pocket and including a top layer of insulative material, a second pocket being provided with a dead air space as additional insulation above the insulative material, and a top laminate being positioned above the second pocket. The bottom, middle and top laminates each have outer peripheral edges that are bonded together by a radio frequency (RF) heat-sealing step. A method is also disclosed for manufacturing the compress.

8 Claims, 2 Drawing Sheets

REUSABLE AND MICROWAVABLE HOT INSULATED COMPRESS AND METHOD OF MANUFACTURE

BACKGROUND OF THE INVENTION

1. Field of the Invention

The present invention relates to a therapeutic compress and, in particular, to a reusable and microwavable hot insulated compress. The invention also relates to a method for manufacturing such a compress.

2. Description of the Related Art

Heat therapy is a recommended treatment for relieving minor pain caused by muscle aches, soreness, stiffness, cramps, and arthritis. The therapy works by providing heat through the skin to the affected muscles to dilate the blood vessels therein and, thus, to increase the circulation of the blood therethrough. For many years, this heat therapy has been provided via a hot compress which has held against the affected portion of the body.

Subsequently, manufacturers developed compresses that could serve to provide either hot or cold therapy. Cold therapy is a recommended treatment for relieving minor pain caused by injuries to muscles which swell in response to such injuries. This cold therapy works by withdrawing heat through the skin from the injured muscles to constrict the blood vessels therein and, thus, to reduce swelling by decreasing the circulation of the blood through such injured muscles. Such a cold therapy pack is shown in U.S. Pat. No. 4,243,041 which issued to Malcolm D. Paul on Jan. 6, 1981.

Examples of compresses that serve to provide either hot or cold therapy are the prior art packs shown in the following references:

| Country | Patent No. | Inventor(s) | Issue Date |
| --- | --- | --- | --- |
| U.S. | 3,763,622 | Stanley, Jr. | Oct. 09, 1973 |
| U.S. | 3,780,537 | Spencer | Dec. 25, 1973 |
| U.S. | 3,804,077 | Williams | Apr. 16, 1974 |
| U.K. | 1,383,536 | Turner | Feb. 12, 1975 |
| U.S. | 3,874,504 | Verakas | Apr. 01, 1975 |
| U.S. | 3,885,403 | Spencer | May 27, 1975 |
| U.S. | 3,893,834 | Armstrong | July 08, 1975 |
| U.S. | 4,055,188 | Pelton | Oct. 25, 1977 |
| U.S. | 4,092,982 | Salem | June 06, 1978 |
| U.S. | 4,114,620 | Moore et al. | Sep. 19, 1978 |
| U.S. | 4,381,025 | Schooley | Apr. 26, 1983 |
| U.S. | 4,462,224 | Dunshee et al. | July 31, 1984 |
| U.S. | 4,596,250 | Beisang, III et al. | June 24, 1986 |

More recently, some compresses have been made microwavable so that they may be available more quickly than conventional compresses which need to be either boiled or frozen before they are ready for use. Such microwavable compresses are shown in the following U.S. Patents:

| U.S. Pat. No. | Inventor(s) | Issue Date |
| --- | --- | --- |
| 4,488,552 | McCann et al. | Dec. 18, 1984 |
| 4,671,267 | Stout | June 09, 1987 |
| 4,756,311 | Francis, Jr. | July 12, 1988 |

However, such prior art compresses, either hot or cold or dual in nature, are usually made with thin plastic, such as polyethylene, which is clammy to touch and has an uncomfortable feeling for the user. Also, because their outer walls are usually very thin, such prior art compresses are often too hot to handle after they are first heated. Consequently, the user is required to hold such a hot compress against the sore muscle area with either a towel, or a paper cloth, or like. Holding the hot compress in this manner is cumbersome and often results in slippage of the hot compress away from the muscle area. Occasionally, such slippage will result in a fall that will rupture the outer walls of the compress, thus spilling the fluid contents thereof. Accordingly, there is a distinct disadvantage in using current state-of-the art hot compresses.

SUMMARY OF THE INVENTION

It is a primary object of the present invention to provide a reusable and microwavable hot compress which has an intermediate insulative layer that allows a user to handle the compress easily when such a compress is hot and ready to be applied to a sore muscle area.

It is another object of the present invention to provide a method of manufacturing such a compress with an intermediate insulative layer and a dead air space on one side of a gel-filled space so that the user's hand is not burned between applications when holding the heated compress against the sore muscle area.

These and other objects and advantages of the present invention will become readily apparent from a study of the following brief description of the drawings and the subsequent detailed description of the preferred embodiment.

DETAILED DESCRIPTION OF THE PREFERRED EMBODIMENT

Figure 1:
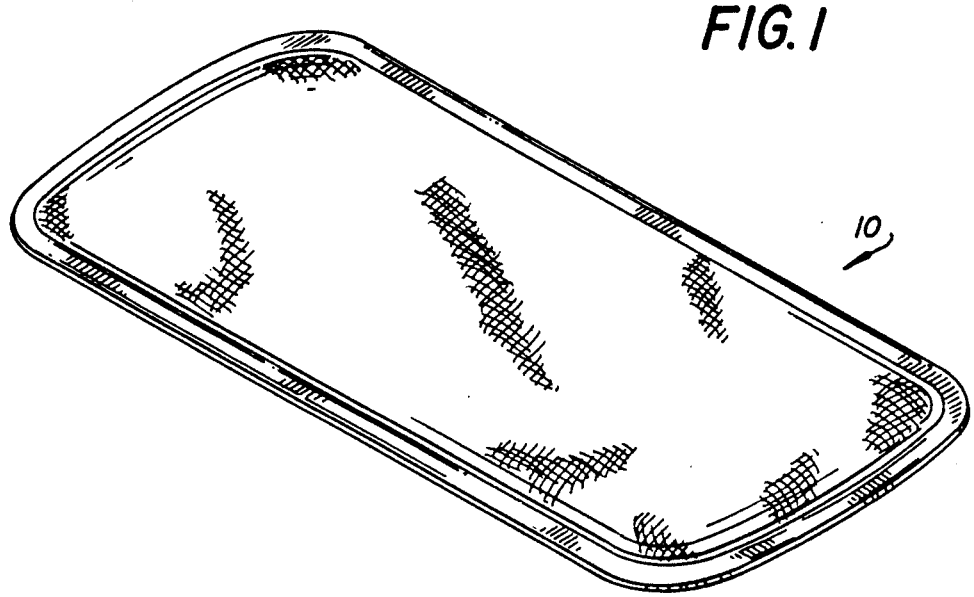
FIG. 1 is a perspective view of the compress of the present invention.

In FIG. 1 of the drawings, there is shown a perspective view of a compress 10 of the present invention.

Figure 2:
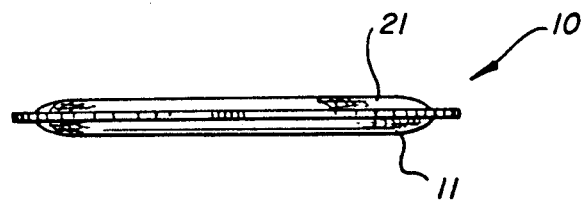
FIG. 2 is a short side elevational view of the compress of the present invention.

In FIG. 2, an elevational view of a short side of the compress 10 is shown. A first bottom layer 11 of polyester fabric is eight to ten mils thick and a second top layer 21 of polyester fabric is also eight to ten mils thick.

Figure 3:
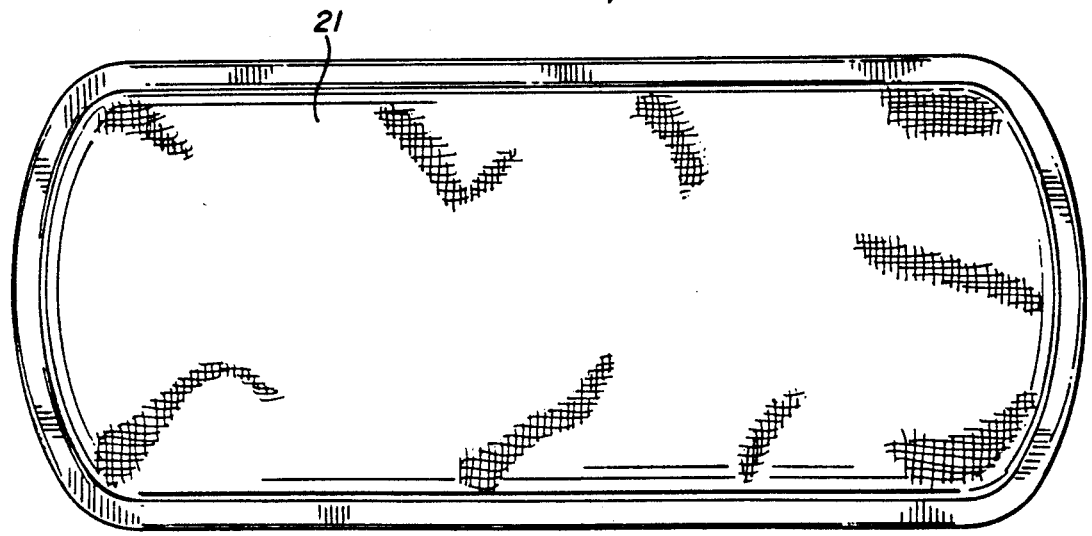
FIG. 3 is a top plan view of the compress of the present invention.

In FIG. 3, a top plan view of the compress 10 is shown with only the second top layer 21 of polyester fabric being visible. A bottom plan view showing only the first bottom layer 11 of polyester fabric would be identical to this top plan view of the compress 10.

Figure 4:
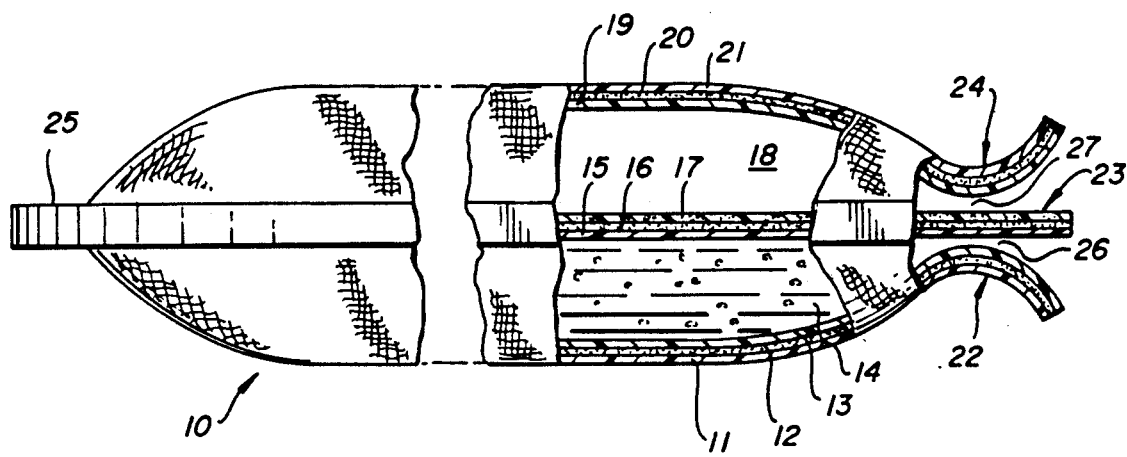
FIG. 4 is a partially broken away and enlarged cross-sectional view of the short side of the compress shown in FIG. 2.

In FIG. 4, the short side of the compress 10 shown in FIG. 2 is partially broken away and enlarged to illustrate the various layers of the invention in cross-section. The view of the layers in FIG. 4 will be discussed from bottom to top with the bottom layer intended to be applied next to the affected body part.

In FIG. 4, the first bottom layer 11 is made of polyester fabric, as indicated previously in the discussion of FIG. 2. Next, there is a first bottom layer 12 of plastisol adhesive that is spread very thinly on a top surface of the layer 11 of polyester fabric. Then, a first bottom layer 13 of vinyl plastic 10 to 12 mils thick is laid on top of the layer 12 of the plastisol adhesive so that the layer 13 of vinyl plastic adheres to the layer 11 of polyester fabric.

A gel 14 is later placed into a first pocket provided above the layer 13 inside the compress 10. The first pocket is formed by a top surface of the first layer 13 of vinyl plastic and by a bottom surface of a second layer 15 of vinyl plastic. Both freezable and heatable gels are known in the prior art. The heatable gel 14 used in the preferred embodiment of the present invention includes about 73 to 77 percent distilled water by weight, about 22 to 24 percent boiling point elevator by weight, and about one to five percent thickening agent by weight. The preferred boiling point elevator is propylene glycol which is often used in cosmetics and foods. The preferred thickening agent is an acrylic acid polymer powder, such as Carbopol 940, manufactured by B. F. Goodrich Co. Other ingredients to suppress bacterial growth within the gel 14 and to enhance either processibility or shelf life may be added in amounts varying from one to four percent by weight, depending upon the combination of distilled water, boiling point elevator, and thickening agent.

The second middle layer 15 of vinyl plastic is provided with its bottom surface immediately above the pocket containing the gel and is adjacent to the gel 14 in the compress 10. A second middle layer 16 of plastisol adhesive is spread very thinly on a top surface of the layer 15 of vinyl plastic. Next, a sole layer 17 of open-celled insulative polyester foam is placed on top of the layer 16 of plastisol adhesive so that the layer 17 of insulative foam adheres to the layer 15 of vinyl plastic.

Next, a dead air space 18 is provided in a second pocket as an additional insulation above the layer 17 of insulative foam in the compress 10. The second pocket is formed by a top surface of the layer 17 of insulative foam and by a bottom surface of a third layer 19 of vinyl plastic. The third top layer 19 of vinyl plastic is provided with its bottom surface immediately above and adjacent to the dead air space 18. A third top layer 20 of plastisol adhesive is spread very thinly onto a top surface of the layer 19 of vinyl plastic. Finally, the second top layer 21 of polyester fabric is placed on the layer 20 of plastisol adhesive so that the layer 21 of polyester fabric adheres to the layer 19 of vinyl plastic. As indicated previously in the discussion of FIG. 2, the layer 21 is eight to ten mils thick.

In the process for manufacturing the compress 10, as can be readily seen from the right-hand side of FIG. 4, the first layer 11 of polyester fabric is either bonded or laminated together with the first layer 13 of vinyl plastic by the first layer 14 of plastisol adheseive to form a bottom laminate 22.

Likewise, the second layer 15 of vinyl plastic is either bonded or laminated together with the sole layer 17 of insulative foam by the second layer 16 of plastisol adhesive to form a middle laminate 23.

Similarly, the third layer 19 of vinyl plastic is either bonded or laminated together with the second layer 21 of polyester fabric by the third layer 20 of plastisol adhesive to form a top laminate 24.

In the next step of the process for manufacturing the compress 10, the bottom laminate 22, the middle laminate 23, and the top laminate 24 are cut to size and heat-sealed together to form a coplanar outer edge 25, best seen on the left-hand side of FIG. 4, for the compress 10.

The heat sealing of the three laminates 22, 23 and 24 together to form the outer edge 25 is accomplished by radio-frequency (hereinafter RF) heating which essentially heats the internal molecular structure of the various plastic layers at 27.12 megahertz to cause an outer portion of each plastic layer to melt into the interstices of the fabric and foam layers without scorching the outer surfaces of such fabric and foam layers. In the known prior art methods, various heat-sealing processes are known to scorch occasionally any fabric layers. The avoidance of scorching is an important advantage of the manufacturing process of the present invention over known prior art methods. In other words, the outer edge 25 of the compress is formed by the RF heat-sealing of all coextensive plastic layers 13, 15 and 19 so that they melt into the bottom fabric layer 11, the insulative foam layer 17, and the top fabric layer 21, respectively.

This heat-sealing step is carried out around substantially the entire periphery of the outer edge 25 except for two openings 26 and 27 which are left at one end of the compress 10. These two openings 26 and 27 form entrances into the first and second pockets, respectively, and are seen on the right-hand side of FIG. 4. Through opening 26, the gel 14 is squirted into the first pocket in the compress 10. Through opening 27, air is pumped into the second pocket that provides the dead space 18 inside the compress 10. The squirting of the gel 14 into the first pocket and the pumping of the air into the space 18 are steps that may be carried out either separately or simultaneously during the manufacturing process.

The final step of the method of the present invention involves RF heat-sealing by the openings 26 and 27 so that the gel 14 and the dead air in the space 18 are sealed inside the compress 10.

As a result of the last two manufacturing steps of creating the dead air space 18 and closing the opening 27 with RF heat, the compress 10 is provided with a distinct advantage over the prior art when considered in conjunction with the earlier manufacturing step of laminating the layer 17 of insulative foam into the middle laminate 23 inside the compress 10. This advantage is that the top layer 21 is cooler than the gel 14, even after microwaving.

Figure 5:
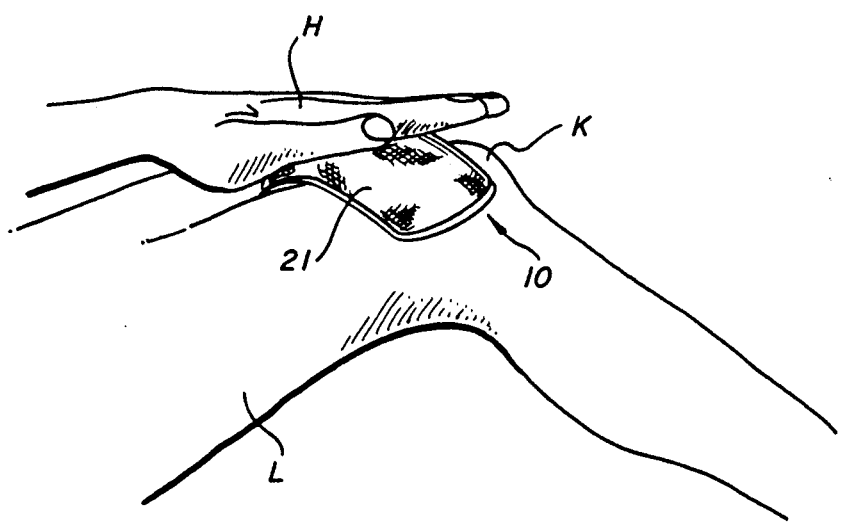
FIG. 5 is a pictorial view illustrating one method of using the compress of the present invention.

This advantage is best realized when viewing FIG. 5 in which the compress 10 is held by a user's hand H on the topmost layer 21 so that heat is radiated into an affected part of the user's body, e.g. in this case an injured knee K of the user's leg L, without the need for any towels, paper cloths, and the like, which are likely to allow slippage of the compress 10 onto the ground or floor.

Before use of the present invention, as shown in FIG. 5, a person will be able to tell the coolest top layer 21 from the bottom layer 11, seen only in FIGS. 2 and 4, because the manufacturer will have either clearly marked the coolest top layer 21 to be held by the user's hand H or color-coded the same coolest top layer 21 so that the layer 21 can be easily distinguished from the hot bottom layer 11. For example, such color coding may involve the use of red ink or dye to indicate the hot bottom layer 11 and the use of blue ink or dye to indicate the coolest top layer 21.

There are several other features that make the present invention more advantageous than known prior art devices. First, the compress 10 made by the above-described manufacturing method uses layered plastic and fabric materials that are designed to be expandable to allow for the escape of steam through the layers 11, 12 and 13 during the microwave heating of the compress 10. In other words, the layers 11-13 are permeable to water vapor because the microscopic interstices function as pinholes to allow the release of steam from the heated gel 14, thus acting as a safety feature in the event that the user inadvertently overheats the compress 10 either in the microwave oven or during heating in a conventional oven.

For example, the prior art compress which is the subject of U.S. Pat. No. 4,756,311 to Francis, Jr., is specifically claimed as a gel pack that does "not pass steam produced during heating. . . by microwave energy". Experiments have shown and it is tacitly admitted by the inventor that this particular prior art compress is unfortunately likely to explode if heated in a microwave oven for more than four minutes.

A second advantageous feature of the present invention is that the layer 17 of insulative foam and the dead air space 18 together function to prevent heat loss from the microwaved hot gel 14. Furthermore, they jointly serve to reflect the heat radiating from the hot gel 14 into the affected portion of the user's body, such as the knee K shown in FIG. 5.

A third advantageous feature of the present invention is that, because the layer 17 of insulative foam is inside the compress 10 and is adjacent to the dead air space 18, the heat emanating from the microwaved hot gel 14 in a direction lateral to the affected portion of the user's body is reduced much more substantially than known prior art compresses having either an outer insulative layer or a single inner insulative layer. Such known prior art compresses with significant lateral emanation of heat are shown in the following references: U.S. Pat. No. 3,874,504 of Verakas; U.S. Pat. No. 3,893,834 of Armstrong; U.S. Pat. No. 4,596,250 of Beisang, III et al.; and U.K. Patent No. 1,383,536 of Turner.

A fourth advantageous feature of the present invention in that, because the outermost layer 21 is made of polyester fabric, this layer 21 can be easily printed upon in a decorative manner and feels very comfortable to the user's hand H seen in FIG. 5. Known prior art compresses, whether hot or cold, are usually made with outer layers of thin polyethylene plastic that is difficult to print upon and is clammy to touch, thus giving an uncomfortable feeling to the user's hand.

A fifth advantageous feature of the present invention is that, because the outermost layer 21 is made of 70-denier interlocked or nonwoven polyester fabric which is capable of stretching both widthwise or lengthwise, the heated fabric will not burn the user's skin, even if applied immediately after removal of the compress 10 from the microwave oven. Because the layer 21 of fabric is expandable, this fabric allows the compress 10 "to breathe" and to have a cool outermost layer 21 which is the only layer to come into direct contact with the user's skin.

A sixth advantageous feature of the present invention is that, because the outermost layer 21 is made of breathable fabric eight to ten mils thick, which is twice the normal thickness of most prior art compresses, the sole middle layer 17 of insulation open-cell foam can be substantially reduced in thickness, i.e. compressed, thus reducing the bulk of the entire compress 10 and lowering the packaging costs thereof. In most prior art compresses that have any kind of insulative layer, the outermost layer is usually nonbreathable plastic, thus requiring the insulative layer to be very thick and rendering the compresses very expensive to package, due to their bulk and the amount of air entrapped therein. Such thick insulative layers are shown in U.S. Pat. No. 4,596,250 to Beisang, III et al. and in U.K. Patent No. 1,383,536 to Turner.

The foregoing preferred embodiment is considered illustrative only. Numerous other modifications will readily occur to those persons skilled in this particular technology after reading this specification. Consequently, the disclosed invention is not limited to the exact structure and manufacturing method shown and described above, but rather is defined by the claims appended hereto.

What we claim as our invention is as follows:

1. A compress comprising:
    a first layer of fabric having a top surface;
    a first layer of adhesive spread on the top surface of the first layer of fabric;
    a first layer of plastic adhered to the top surface of the first layer of fabric by the first layer of adhesive;
    a gel contained in a pocket above the first layer of plastic;
    a second layer of plastic being positioned above the pocket containing the gel, said second layer of plastic having a top surface;
    a second layer of adhesive spread on the top surface of the second layer of plastic;
    a layer of insulative material adhered to the top surface of the second layer of plastic by the second layer of adhesive;
    sealed off pocket means for providing a dead air space as additional insulation above the layer of insulative material;
    a third layer of plastic positioned above the pocket means for providing the dead air space as additional insulation, said third layer of plastic having a top surface;
    a third layer of adhesive spread on the top surface of the third layer of plastic; and
    a second layer of fabric adhered to the top surface of the third layer of plastic by the third layer of adhesive.

2. The compress, according to claim 1, wherein:
    said first layer of fabric, said first layer of adhesive, and said first layer of plastic together form a bottom laminate below the gel contained in the pocket.

3. The compress, according to claim 1, wherein:
    said second layer of plastic, said second layer of adhesive, and the layer of insulative material together form a middle laminate between the gel and the pocket means for providing the dead air space.

4. The compress, according to claim 1, wherein:
    said third layer of plastic, said third layer of adhesive, and said second layer of fabric together form a top laminate above the pocket means for providing the dead air space as additional insulation.

5. A method of manufacturing a compress, comprising the steps of:
    providing a first layer of fabric having a top surface;
    spreading a first layer of adhesive on the top surface of the first layer of fabric;
    adhering a first layer of plastic to the top surface of the first layer of fabric by the first layer of adhesive;
    containing a gel in a pocket arranged above the first layer of plastic;
    positioning a second layer of plastic above the pocket containing the gel, said second layer of plastic having a top surface;

spreading a second layer of adhesive onto the top surface of the second layer of plastic;

adhering a layer of insulative material to the top surface of the second layer of plastic by the second layer of adhesive;

providing a sealed off pocket means with dead air space as additional insulation above the layer of insulative material;

positioning a third layer of plastic above the sealed off pocket means provided with dead air space as additional insulation, said third layer of plastic having a top surface;

spreading a third layer of adhesive onto the top surface of the third layer of plastic; and adhering a second layer of fabric to the top surface of the third layer of plastic by the third layer of adhesive.

6. The method, according to claim 5, comprising the further step of:

bonding together preliminarily the first layer of fabric, the first layer of adhesive, and the first layer of plastic to form a bottom laminate below the pocket containing the gel.

7. The method, according to claim 5, comprising the further step of:

bonding together preliminarily the second layer of plastic, the second layer of adhesive, and the layer of insulative material to form a middle laminate between the pocket containing the gel and the sealed off pocket means provided with dead air space as additional insulation.

8. The method, according to claim 5, comprising the further step of:

bonding together preliminarily the third layer of plastic, the third layer of adhesive, and the second layer of fabric to form a top laminate above the sealed off pocket means for providing the dead air space as additional insulation.

* * * * *

UNITED STATES PATENT AND TRADEMARK OFFICE
CERTIFICATE OF CORRECTION

PATENT NO. : 5,035,241

DATED : July 30, 1991

INVENTOR(S) : Walasek et al.

It is certified that error appears in the above-identified patent and that said Letters Patent is hereby corrected as shown below:

Col. 2, line 10, change "the art" to --the-art--; and
          line 21, change "space" to --pocket--.

Col. 3, line 51, change "adheseive" to --adhesive--.

Col. 4, line 31, change "by" to --of--.

Col. 5, line 60, change "insulation" to --insulative--.

Col. 6, line 29, in claim 1, change "sealed off" to --sealed-off--;
          line 32, in claim 1, after "the", insert --sealed-off--;
          line 49, in claim 3, after "the" (second occurrence), insert --sealed-off--; and
          line 54, in claim 4, after "the" (first occurrence), insert --sealed-off--.

Col. 7, line 6, in claim 5, change "sealed off" to --sealed-off--; and
          line 9, in claim 5, change "sealed" to --sealed- --.

UNITED STATES PATENT AND TRADEMARK OFFICE
CERTIFICATE OF CORRECTION

PATENT NO. : 5,035,241
DATED : July 30, 1991
INVENTOR(S) : Walasek et al.

It is certified that error appears in the above-identified patent and that said Letters Patent is hereby corrected as shown below:

Col. 8, line 11, in claim 7, change "sealed off" to --sealed-off--; and line 18, in claim 8, change "sealed off" to --sealed-off--.

Signed and Sealed this

Twenty-first Day of July, 1992

Attest:

DOUGLAS B. COMER

*Attesting Officer*   *Acting Commissioner of Patents and Trademarks*